(12) United States Patent
Phan et al.

(10) Patent No.: US 6,953,782 B2
(45) Date of Patent: *Oct. 11, 2005

(54) 11-C-SUBSTITUTED ERYTHROMYCIN DERIVATIVES

(75) Inventors: Ly Tam Phan, Quincy, MA (US); Yat Sun Or, Watertown, MA (US); Jay Judson Farmer, New Haven, CT (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/745,856

(22) Filed: Dec. 24, 2003

(65) Prior Publication Data

US 2005/0143326 A1 Jun. 30, 2005

(51) Int. Cl.[7] .................. A61K 31/70; C07H 17/08

(52) U.S. Cl. ..................... 514/29; 536/7.2; 536/7.3

(58) Field of Search .................... 514/29; 536/7.2, 536/7.3, 7.4

(56) References Cited

U.S. PATENT DOCUMENTS

| 3,660,376 A | 5/1972 | Massey et al. |
| 4,847,242 A | 7/1989 | Davies |
| 4,990,602 A | 2/1991 | Morimoto et al. |
| 5,403,923 A | 4/1995 | Kashimura et al. |
| 5,444,051 A | 8/1995 | Agouridas et al. |
| 6,395,710 B1 * | 5/2002 | Chu et al. .................. 514/29 |
| 2003/0125266 A1 | 7/2003 | Chu et al. |
| 2004/0002464 A1 | 1/2004 | Phan et al. |
| 2004/0006027 A1 | 1/2004 | Phan et al. |

FOREIGN PATENT DOCUMENTS

| WO | WO 98/30574 | 7/1998 |
| WO | WO 03/004509 | 1/2003 |
| WO | WO 03/047600 | 6/2003 |

* cited by examiner

*Primary Examiner*—Elli Peselev
(74) *Attorney, Agent, or Firm*—Elmore, Craig & Vanstone, P.C.; Darlene A. Vanstone; Carolyn S. Elmore

(57) ABSTRACT

The present invention discloses compounds of formulae I, II, III or IV or pharmaceutically acceptable salts, esters, or prodrugs thereof:

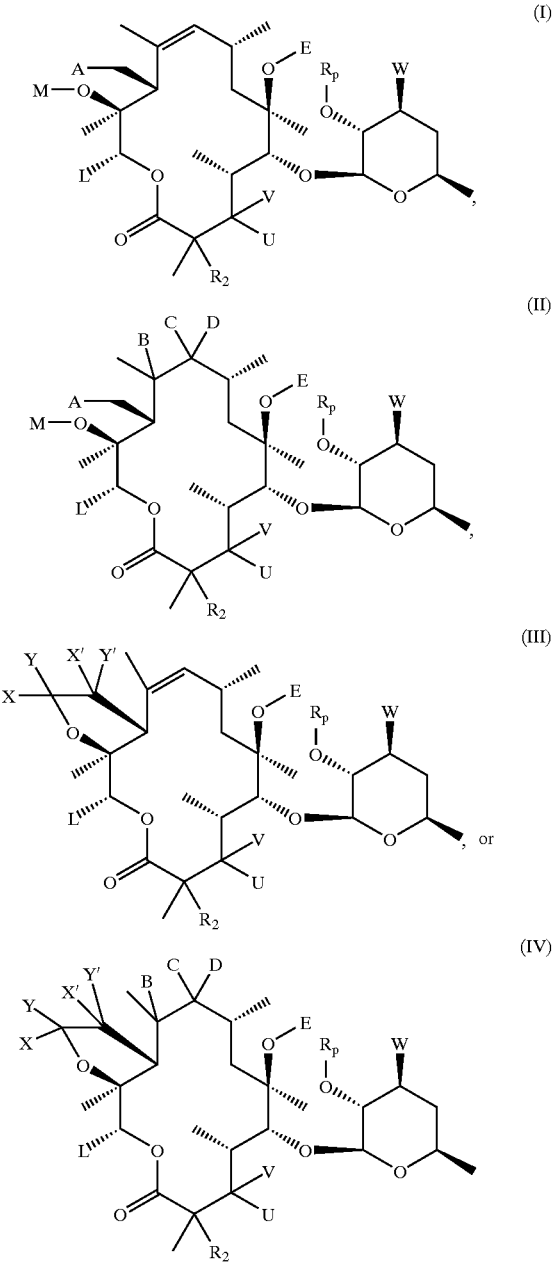

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

15 Claims, No Drawings

11-C-SUBSTITUTED ERYTHROMYCIN DERIVATIVES

TECHNICAL FIELD

The present invention relates to novel macrolides having antibacterial activity and useful in the treatment and prevention of bacterial infections. More particularly, the invention relates to a novel class of 11-C-substituted erythromycin derivatives, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin and clarithromycin.

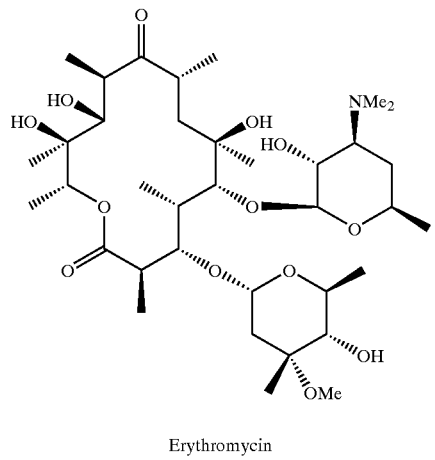

Erythromycin

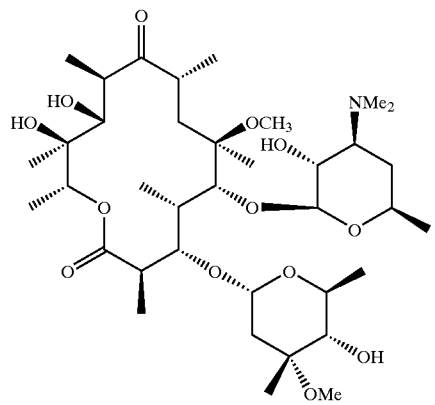

Clarithromycin

The search for macrolides active against MLS$_B$-resistant strains (MLS$_B$=Macrolides-Lincosamides-type B Streptogramines) has become a major goal, together with retaining the overall profile of the macrolides in terms of stability, tolerance and pharmacokinetics.

The present invention provides a novel class of 11-C-substituted erythromycin derivatives which possess antibacterial activity.

In one aspect of the present invention there are provided novel erythromycin derivatives represented by the formulae as illustrated below:

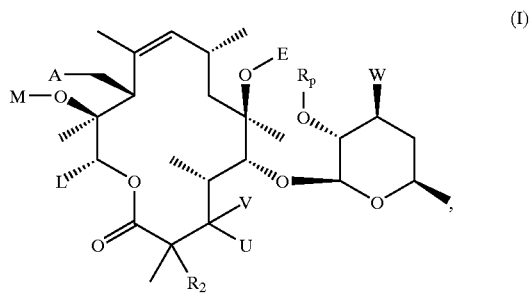

(I)

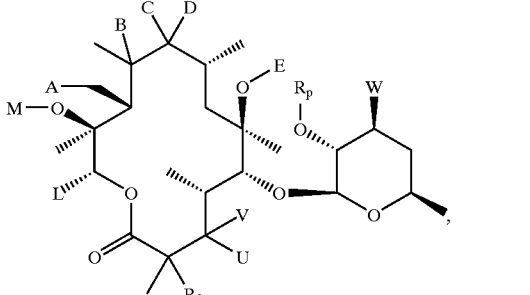

(II)

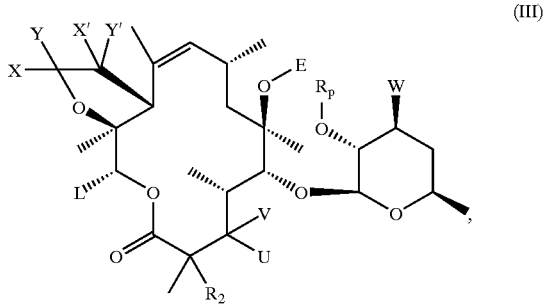

(III)

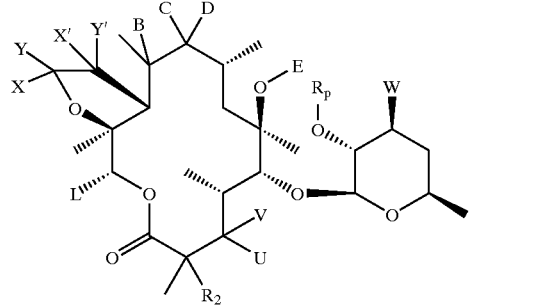

(IV)

or their racemates, enantiomers, regioisomers, salts, esters or prodrugs thereof, wherein A is independently selected from $R_1$, —CH($R_{A1}$)($R_{A2}$);

Each B, C, and D is independently selected from deuterium, halogen, $R_1$, $OR_1$, $S(O)_nR_1$, —$NR_1C(O)R_1$, —$NR_1C(O)NR_3R_4$, —$NR_1S(O)_nR_1$, —$C(O)NR_3R_4$, and —$NR_3R_4$;

or B and C taken together are selected from —O—, —S—, —N($R_1$)—, a substituted or unsubstituted alicyclic group, or a substituted or unsubstituted heterocyclic group;

or C and D taken together with the carbon atom to which they are attached are selected CO, C=CHR$_1$, C=NR$_1$, C=NOR$_1$, C=NO(CH$_2$)$_m$R$_1$, C=NNHR$_1$, C=NNHCOR$_1$, C=NNHCONR$_3$R$_4$, C=NNHS(O)$_n$R$_1$, C=N—N=CHR$_1$;

E is independently selected from R$_1$;

Each R$_1$ is independently selected from the group consisting of: hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

Each of R$_3$ and R$_4$ is independently selected from the group consisting of: hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a substituted, or unsubstituted heterocyclic group; or can be taken together with the nitrogen atom to which they are attached to form a substituted or unsubstituted heterocyclic or heteroaromatic ring;

Each R$_{A1}$ and R$_{A2}$ are independently selected from hydrogen, deuterium, halogen, R$_1$, OR$_1$, S(O)$_n$R$_1$, —NR$_1$C(O)R$_1$, —NR$_1$C(O)NR$_3$R$_4$, —NHS(O)$_n$R$_1$, —CONR$_3$R$_4$, and NR$_3$R$_4$;

or R$_{A1}$ and R$_{A2}$, taken together with the carbon atom to which they are attached, form a substituted or unsubstituted alicyclic, aromatic, heterocyclic or heteroaromatic ring;

or R$_{A1}$ and R$_{A2}$ taken together with the carbon atom to which they are attached are selected from C=O, C=CHR$_1$, C=NR$_1$, C=NOR$_1$, C=NO(CH$_2$)$_m$R$_1$, C=NNHR$_1$, C=NNHCOR$_1$, C=NNHCONR$_3$R$_4$, C=NNHS(O)$_n$R$_1$, C=N—N=CHR$_1$;

M is selected from the group consisting of: R$_1$, C(O)R$_1$, S(O)$_n$R$_1$, or C(O)NR$_3$R$_4$;

L is selected from the group consisting of: hydrogen, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

X, Y, X', and Y' are independently selected from the group consisting of: deuterium, halogen, R$_1$, OR$_1$, S(O)$_n$R$_1$, —NR$_1$C(O)R$_1$, —NR$_1$C(O)NR$_3$R$_4$, —NR$_1$S(O)$_n$R$_1$, —C(O)NR$_3$R$_4$, and —NR$_3$R$_4$;

or X and Y, taken together with the carbon atom to which they are attached, are C=O;

or X and X', taken together with the carbon atoms to which they are attached, are C=C;

one of U or V is hydrogen and the other is independently selected from the group
consisting of: R$_1$, OR$_1$, OC(O)R$_1$, OC(O)NR$_3$R$_4$, S(O)$_n$R$_1$, or

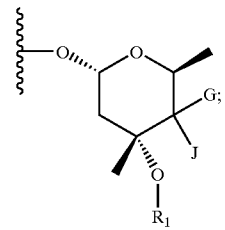

or U and V, taken together with the carbon atom to which they are attached, are C=O;

one of J or G is hydrogen and the other is selected from: R$_1$, OR$_1$, or NR$_3$R$_4$;

or, J and G, taken together with the carbon atom to which they are attached, are selected from: C=O, C=NR$_1$, C=NOR$_1$, C=NO(CH$_2$)$_m$R$_1$, C=NNHR$_1$, C=NNHCOR$_1$, C=NNHCONR$_1$R$_2$, C=NNHS(O)$_n$R$_1$, or C=N—N=CHR$_1$;

W is NR$_3$R$_4$;

R$_2$ is selected from hydrogen, alkyl or halogen;

R$_p$ is selected from a hydrogen and a hydroxy protecting group;

m is an integer; and n is 0, 1, or 2.

In another embodiment of the present invention there are disclosed pharmaceutical compositions comprising a therapeutically effective amount of any compound of the present invention in combination with a pharmaceutically acceptable carrier or excipient. In yet another embodiment of the invention are methods of treating antibacterial infections in a subject with said pharmaceutical compositions. Suitable carriers and methods of formulation are also disclosed.

In a further aspect of the present invention there are provided processes for the preparation of any erythromycin derivative of formulas I, II, III, or IV via any synthetic route delineated herein.

DETAILED DESCRIPTION OF THE INVENTION

Representative subgenera of the present invention are:

A compound of formula I or II, wherein E is not methyl;

A compound of formula I, II, III, or IV, wherein E is hydrogen;

A compound of formula I or II, wherein A is CHO;

A compound of formula III or IV, wherein X is hydrogen, Y is hydroxyl and Z is hydrogen;

A compound of formula I, II, III, or IV, wherein C and D taken together with the carbon atom to which they are attached are C=O;

A compound of formula III or IV, wherein X and Y taken together with the carbon atom to which they are attached are C=O;

A compound of formula I, II, III, or IV, wherein E is CH$_2$CH=CH$_2$;

A compound of formula I, II, III, or IV, wherein W is N(CH$_3$)$_2$;

A compound of formula I, II, III, or IV, wherein L is ethyl; or

A compound of formula I, II, III, or IV, wherein U and V taken together with the carbon atom to which they are attached are C=O.

Representative compounds of the present invention are:

Compound of formula I: A is CHO, M, E, R$_p$, and R$_2$ are hydrogen, and U and V taken together with the carbon atom to which they are attached are C=O;

Compound of formula I: A is CH$_2$OH, M, E, R$_p$, and R$_2$ are hydrogen, and U and V taken together with the carbon atom to which they are attached are C=O;

Compound of formula I: A is CH$_2$OCO-[3-quinolyl], M, E, R$_p$, and R$_2$ are hydrogen, and U and V taken together with the carbon atom to which they are attached are C=O;

Compound of formula I: A is CH$_2$OCO-[4-quinolyl], M, E, R$_p$, and R$_2$ are hydrogen, and U and V taken together with the carbon atom to which they are attached are C=O;

Compound of formula I: A is CH=CH-phenyl, M, E, R$_p$, and R$_2$ are hydrogen, and U and V taken together with the carbon atom to which they are attached are C=O;

Compound of formula I: A is CH$_2$NH-benzyl, M, E, R$_p$, and R$_2$ are hydrogen, and U and V taken together with the carbon atom to which they are attached are C=O;

Compound of formula I: A is $CH_2NH$-allyl, M, E, $R_p$, and $R_2$ are hydrogen, and U and V taken together with the carbon atom to which they are attached are C=O;

Compound of formula II: A is CHO, B is hydrogen, C is hydrogen, D is hydrogen, M, E, $R_p$, and $R_2$ are hydrogen, and U and V taken together with the carbon atom to which they are attached are C=O;

Compound of formula II: A is CHO, B and C taken together are —O—, B is hydrogen, M, E, $R_p$, and $R_2$ are hydrogen, and U and V taken together with the carbon atom to which they are attached are C=O;

Compound of formula II: A is CHO, B and C taken together with the carbon atom to which they are attached are C=O, D is hydrogen, M, E, $R_p$, and $R_2$ are hydrogen, and U and V taken together with the carbon atom to which they are attached are C=O;

Compound of formula II: A is CHO, B is OH, C is hydrogen, D is OH, M, E, $R_p$, and $R_2$ are hydrogen;

Compound of formula II: A is $CH_2OH$, B is hydrogen, C is hydrogen, D is hydrogen, M, E, $R_p$, and $R_2$ are hydrogen, and U and V taken together with the carbon atom to which they are attached are C=O;

Compound of formula II: A is $CH_2OH$, B and C taken together are —O—, C is hydrogen, M, E, $R_p$, and $R_2$ are hydrogen, and U and V taken together with the carbon atom to which they are attached are C=O;

Compound of formula II: A is $CH_2OH$, C and D taken together with the carbon atoms to which they are attached are C=O, B is hydrogen, M, E, $R_p$, and $R_2$ are hydrogen, and U and V taken together with the carbon atom to which they are attached are C=O;

Compound of formula II: A is $CH_2OH$, B is OH, C is hydrogen, D is OH, M, E, $R_p$, and $R_2$ are hydrogen, and U and V taken together with the carbon atom to which they are attached are C=O;

Compound of formula II: A is $CH_2OCO$-[3-quinolyl], B is hydrogen, C is hydrogen, D is hydrogen, M, E, $R_p$, and $R_2$ are hydrogen, and U and V taken together with the carbon atom to which they are attached are C=O;

Compound of formula II: A is $CH_2OCO$-[3-quinolyl], B and C taken together are —O—, C is hydrogen, M, E, $R_p$, and $R_2$ are hydrogen, and U and V taken together with the carbon atom to which they are attached are C=O;

Compound of formula II: A is $CH_2OCO$-[3-quinolyl], C and D taken together with the carbon atom to which they are attached are C=O, B is hydrogen, M, E, $R_p$, and RH are hydrogen;

Compound of formula II: A is $CH_2OCO$-[3-quinolyl], B is OH, C is hydrogen, D is OH, M, E, $R_p$, and $R_2$ are hydrogen, and U and V taken together with the carbon atom to which they are attached are C=O;

Compound of formula II: A is $CH_2OCO$-[4-quinolyl], B is hydrogen, C is hydrogen, D is hydrogen, M, E, $R_p$, and $R_2$ are hydrogen, and U and V taken together with the carbon atom to which they are attached are C=O;

Compound of formula II: A is $CH_2OCO$-[4-quinolyl], B and C taken together are —O—, C is hydrogen, M, E, $R_p$, and $R_2$ are hydrogen, and U and V taken together with the carbon atom to which they are attached are C=O;

Compound of formula II: A is $CH_2OCO$-[4-quinolyl], C and D taken together with the carbon atom to which they are attached are C=O, B is hydrogen M, E, $R_p$, and $R_H$ are hydrogen, and U and V taken together with the carbon atom to which they are attached are C=O;

Compound of formula II: A is $CH_2OCO$-[4-quinolyl], B is OH, C is hydrogen, D is OH, M, E, $R_p$, and $R_2$ are hydrogen, and U and V taken together with the carbon atom to which they are attached are C=O;

Compound of formula II: A is CH=CH-phenyl, B is hydrogen, C is hydrogen, D is hydrogen, M, E, $R_p$, and $R_2$ are hydrogen, and U and V taken together with the carbon atom to which they are attached are C=O;

Compound of formula II: A is $CH_2NH$-benzyl, B is hydrogen, C is hydrogen, D is hydrogen, M, E, $R_p$, and $R_2$ are hydrogen, and U and V taken together with the carbon atom to which they are attached are C=O;

Compound of formula II: A is $CH_2NH$-benzyl, B and C taken together are —O—, C is hydrogen, M, E, $R_p$, and $R_2$ are hydrogen, and U and V taken together with the carbon atom to which they are attached are C=O;

Compound of formula II: A is $CH_2NH$-benzyl, B and C taken together with the carbon atom to which they are attached are C=O, D is hydrogen, M, E, $R_p$, and $R_2$ are hydrogen, and U and V taken together with the carbon atom to which they are attached are C=O;

Compound of formula II: A is $CH_2NH$-benzyl, B is OH, C is hydrogen, D is OH, M, E, $R_p$, and $R_2$ are hydrogen, and U and V taken together with the carbon atom to which they are attached are C=O;

Compound of formula II: A is $CH_2NH$-allyl, B is hydrogen, C is hydrogen, D is hydrogen, M, E, $R_p$, and $R_2$ are hydrogen, and U and V taken together with the carbon atom to which they are attached are C=O;

Compound of formula II: A is $CH_2NH$-allyl, B and C taken together are —O—, C is hydrogen, M, E, $R_p$, and $R_2$ are hydrogen, and U and V taken together with the carbon atom to which they are attached are C=O;

Compound of formula II: A is $CH_2NH$-allyl, C and D taken together with the carbon atom to which they are attached are C=O, B is hydrogen, M, E, $R_p$, and $R_2$ are hydrogen, and U and V taken together with the carbon atom to which they are attached are C=O;

Compound of formula II: A is $CH_2NH$-allyl, B is OH, C is hydrogen, D is OH, M, E, $R_p$, and $R_2$ are hydrogen, and U and V taken together with the carbon atom to which they are attached are C=O; or Compound of formula II or IV: B is OH, C is hydrogen, D is OH, U and V taken together with the carbon atom to which they are attached are C=O, X and Y taken together with the carbon atom to which they are attached are C=O, and M, E, $R_p$, $R_2$, X', and Y' are hydrogen.

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art (such as penicillin, amoxicillin, azithromycin, erythromycin, ciproflaxin, telithromycin, cethromycin, and the like) or a pharmaceutically acceptable salt, ester, or prodrug thereof, with a pharmaceutically acceptable carrier or excipient.

Yet an additional aspect of the present invention relates to a method of treating a subject (e.g., mammal, human, horse, dog, cat, fish) having bacterial infection or disease or disease symptom related to having a bacterial infection (including diseases delineated herein). The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Also within the scope of this invention is a packaged product. The packaged product includes a container, one of the aforementioned compounds in the container, and a legend (e.g., a label or an insert) associated with the container and indicating administration of the compound for treating a disorder associated with bacterial infection, including the diseases delineated herein.

Definitions

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The terms "$C_1$–$C_3$ alkyl," "$C_1$–$C_6$ alkyl," or "$C_1$–$C_{12}$ alkyl," as used herein, refer to saturated, straight- or branched-chain hydrocarbon radicals containing between one and three, one and twelve, or one and six carbon atoms, respectively. Examples of $C_1$–$C_3$ alkyl radicals include methyl, ethyl, propyl and isopropyl radicals; examples of $C_1$–$C_6$ alkyl radicals include, but are not limited to, methyl, ethyl, propyl, propyl, butyl, pentyl, and hexyl radicals; and examples of $C_1$–$C_{12}$ alkyl radicals include, but are not limited to, ethyl, propyl, propyl, hexyl, heptyl, octyl, nonyl, decyl, undecyl, dodecyl radicals and the like.

The term "substituted alkyl," as used herein, refers to an alkyl, such as a $C_1$–$C_{12}$ alkyl or $C_1$–$C_6$ alkyl group, substituted by one, two, three or more aliphatic substituents.

Suitable aliphatic substituents include, but are not limited to, —F, —Cl, —Br, —I, —OH, protected hydroxy, aliphatic ethers, aromatic ethers, oxo, —$NO_2$, —CN, —$C_1$–$C_{12}$-alkyl optionally substituted with halogen (such as perhaloalkyls), $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkynyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkynyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkynyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkynyl, —CONH—$C_3$–$C_{12}$-cycloalkyl, —CONH-aryl, —CONH-heteroaryl, —CONH-heterocycloalkyl, —$CO_2$—$C_1$–$C_{12}$-alkyl, —$CO_2$—$C_2$–$C_{12}$-alkenyl, —$CO_2$—$C_2$–$C_{12}$-alkynyl, —$CO_2$—$C_3$–$C_{12}$-cycloalkyl, —$CO_2$-aryl, —$CO_2$-heteroaryl, —$CO_2$-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkynyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkynyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkynyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkynyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkynyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkynyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkynyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkynyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkynyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkynyl, —S(O)—$C_3$–$C_{12}$-cycloalkyl, —S(O)-aryl, —S(O)-heteroaryl, —S(O)-heterocycloalkyl —$SO_2NH_2$, —$SO_2$NH—$C_1$–$C_{12}$-alkyl, —$SO_2$NH—$C_2$–$C_{12}$-alkenyl, —$SO_2$NH—$C_2$–$C_{12}$-alkynyl, —$SO_2$NH—$C_3$–$C_{12}$-cycloalkyl, —$SO_2$NH-aryl, —$SO_2$NH-heteroaryl, —$SO_2$NH-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkynyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, polyalkoxyalkyl, polyalkoxy, -methoxymethoxy, -methoxyethoxy, —SH, —S—$C_1$–$C_{12}$-alkyl, —S—$C_2$–$C_{12}$-alkenyl, —S—$C_2$–$C_{12}$-alkynyl, —S—$C_3$–$C_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "$C_2$–$C_{12}$ alkenyl" or "$C_2$–$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "$C_2$–$C_{12}$ alkenyl" or "$C_2$–$C_6$ alkenyl" group as previously defined, substituted by one, two, three or more aliphatic substituents.

The terms "$C_2$–$C_{12}$ alkynyl" or "$C_2$–$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$–$C_{12}$ alkynyl" or "$C_2$–$C_6$ alkynyl" group as previously defined, substituted by one, two, three or more aliphatic substituents.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as previously defined, substituted by one, two, three or more aromatic substituents.

Aromatic substituents include, but are not limited to, —F, —Cl, —Br, —O, —OH, protected hydroxy, aliphatic ethers, aromatic ethers, oxo, —NO$_2$, —CN, —$C_1$–$C_{12}$-alkyl optionally substituted with halogen (such as perhaloalkyls), $C_2$–$C_{12}$-alkenyl optionally substituted with halogen, —$C_2$–$C_{12}$-alkynyl optionally substituted with halogen, —NH$_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkynyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkynyl, —C(O)—$C_3$–$C_{12}$-cycloalkyl, —C(O)-aryl, —C(O)-heteroaryl, —C(O)-heterocycloalkyl, —CONH$_2$, —CONH—$C_1$–$C_{12}$-alkyl, —CONH—$C_2$–$C_{12}$-alkenyl, —CONH—$C_2$–$C_{12}$-alkynyl, —CONH—$C_3$–$C_{12}$-cycloalkyl, —CONH-aryl, —CONH-heteroaryl, —CONH-heterocycloalkyl, —CO$_2$—$C_1$–$C_{12}$-alkyl, —CO$_2$—$C_2$–$C_{12}$-alkenyl, —CO$_2$—$C_2$–$C_{12}$-alkynyl, —CO$_2$—$C_3$–$C_{12}$-cycloalkyl, —CO$_2$-aryl, —CO$_2$-heteroaryl, —CO$_2$-heterocycloalkyl, —OCO$_2$—$C_1$–$C_{12}$-alkyl, —OCO$_2$—$C_2$–$C_{12}$-alkenyl, —OCO$_2$—$C_2$–$C_{12}$-alkynyl, —OCO$_2$—$C_3$–$C_{12}$-cycloalkyl, —OCO$_2$-aryl, —OCO$_2$-heteroaryl, —OCO$_2$-heterocycloalkyl —OCONH$_2$, —OCONH—$C_1$–$C_{12}$-alkyl, —OCONH—$C_2$–$C_{12}$-alkenyl, —OCONH—$C_2$–$C_{12}$-alkynyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkynyl, —NHC(O)—$C_3$–$C_{12}$-cycloalkyl, —NHC(O)-aryl, —NHC(O)-heteroaryl, —NHC(O)-heterocycloalkyl, —NHCO$_2$—$C_1$–$C_{12}$-alkyl, —NHCO$_2$—$C_2$–$C_{12}$-alkenyl, —NHCO$_2$—$C_2$–$C_{12}$-alkynyl, —NHCO$_2$—$C_3$–$C_{12}$-cycloalkyl, —NHCO$_2$-aryl, —NHCO$_2$-heteroaryl, —NHCO$_2$-heterocycloalkyl, —NHC(O)NH$_2$, NHC(O)NH—$C_1$–$C_{12}$-alkyl, —NHC(O)NH—$C_2$–$C_{12}$-alkenyl, —NHC(O)NH—$C_2$–$C_{12}$-alkynyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$–$C_{12}$-alkyl, —NHC(S)NH—$C_2$–$C_{12}$-alkenyl, —NHC(S)NH—$C_2$–$C_{12}$-alkynyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$–$C_{12}$-alkyl, —NHC(NH)NH—$C_2$–$C_{12}$-alkenyl, —NHC(NH)NHC$_2$—$C_1$–$C_{12}$-alkynyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkynyl, —NHC(NH)—$C_3$–$C_2$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkynyl, —C(NH)NH—$C_3$–$C_2$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkynyl, —S(O)—$C_3$–$C_{12}$-cycloalkyl, —S(O)-aryl, —S(O)-heteroaryl, —S(O)-heterocycloalkyl —SO$_2$NH$_2$, —SO$_2$NH—$C_1$–$C_{12}$-alkyl, —SO$_2$NH—$C_2$–$C_{12}$-alkenyl, —SO$_2$NH—$C_2$–$C_{12}$-alkynyl, —SO$_2$NH—$C_3$–$C_{12}$-cycloalkyl, —SO$_2$NH-aryl, —SO$_2$NH-heteroaryl, —SO$_2$NH-heterocycloalkyl, —NHSO$_2$—$C_1$–$C_{12}$-alkyl, —NHSO$_2$—$C_2$–$C_{12}$-alkenyl, —NHSO$_2$—$C_2$–$C_{12}$-alkynyl, —NHSO$_2$—$C_3$–$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$–$C_{12}$-cycloalkyl, polyalkoxyalkyl, polyalkoxy, -methoxymethoxy, -methoxyethoxy, —SH, —S—$C_1$–$C_{12}$-alkyl, —S—$C_2$–$C_{12}$-alkenyl, —S—$C_2$–$C_{12}$-alkynyl, —S—$C_3$–$C_{12}$-cycloalkyl, —S-aryl, —S-heteroaryl, —S-heterocycloalkyl, or methylthiomethyl. It is understood that the aryls, heteroaryls, alkyls and the like can be further substituted.

The term "arylalkyl," as used herein, refers to an aryl group attached to the parent compound via a $C_1$–$C_3$ alkyl or $C_1$–$C_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The terms "heteroaryl" or "heteroaromatic," as used herein, refers to a mono-, bi-, or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The term "substituted heteroaryl," as used herein, refers to a heteroaryl group as previously defined, substituted by one, two, three or four aromatic substituents.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl.

The term "substituted alicyclic" group as previously defined, substituted by one, two, three or more aliphatic substituents.

The terms "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocyclic," as used herein, refers to a heterocyclic group, as previously defined, substituted by one, two, three or more aliphatic substituents.

The term "heteroarylalkyl," as used herein, to an heteroaryl group attached to the parent compound via a $C_1$–$C_3$ alkyl or $C_1$–$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "$C_1$–$C_3$-alkylamino," as used herein, refers to one or two $C_1$–$C_3$-alkyl groups, as previously defined, attached to the parent molecular moiety through a nitrogen atom. Examples of $C_1$–$C_3$-alkylamino include, but are not limited to, methylamino, dimethylamino, ethylamino, diethylamino, and propylamino.

The term "alkylamino" refers to a group having the structure —NH($C_1$–$C_{12}$ alkyl) where $C_1$–$C_{12}$ alkyl is as previously defined.

The term "dialkylamino" refers to a group having the structure —N($C_1$–$C_{12}$ alkyl) ($C_1$–$C_{12}$ alkyl), where $C_1$–$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$–$C_{12}$ alkyl) or —C(O)N($C_1$–$C_{12}$ alkyl) ($C_1$–$C_{12}$ alkyl), —C(O)NH$_2$, NHC(O)($C_1$–$C_{12}$ alkyl), N($C_1$–$C_{12}$ alkyl)C(O)($C_1$–$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bn or —C(O)C$_6$H$_5$), and trimethylsilyl (TMS or-Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1–19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991); Bundgaard, et al., Journal of Drug Deliver Reviews, 8:1–38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating bacterial infections through administering, pharmaceutically acceptable prodrugs of compounds of the formula I. For example, compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*, or *Peptostreptococcus* spp. *Pseudomonas* spp.; pharyngitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C-F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Nesseria gonorrheae*; toxin diseases related to infection by *S. aureus* (food poisoning and Toxic shock syndrome), or Groups A, S. and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus*, Propionibacterium acne; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica., P. multocida, Mycoplasma bovis*, or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae., P. multocida*, or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylo-* bacter spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al.,"The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate Mueller Hinton Broth medium (CAMlB) for the observed bacterial isolates. Antimicrobial agents are serially diluted (2-fold) in DMSO to produce a concentration range from about 64 $\mu$g/ml to about 0.03 $\mu$g/ml. The diluted compounds (2 $\mu$l/well) are then transferred into sterile, uninoculated CAMHB (0.2 mL) by use of a 96 fixed tip-pipetting station. The inoculum for each bacterial strain is standardized to $5\times10^5$ CFU/mL by optical comparison to a 0.5 McFarland turbidity standard. The plates are inoculated with 10 $\mu$l/well of adjusted bacterial inoculum. The 96 well plates are covered and incubated at 35+/–2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 $\mu$g/ml to about 0.03 $\mu$g/ml.

All in vitro testing follows the guidelines described in the Approved Standards M7-A4 protocol, published by the National Committee for Clinical Laboratory Standards (NCCLS).

Pharmaceutical Compositions.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
AIBN for azobisisobutyronitrile;
Bu$_3$SnH for tributyltin hydride;
CDI for carbonyldiimidazole;
dba for dibenzylidene acetone;
dppb for diphenylphosphino butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;

EtOAc for ethyl acetate;

MeOH for methanol;

Ms for mesylate or O—SO$_2$—CF$_3$;

NaN(TMS)$_2$ for sodium bis(trimethylsilyl)amide;

NMMO for N-methylmorpholine N-oxide;

TEA for triethylamine;

THF for tetrahydrofuran;

TPP or PPh$_3$ for triphenylphosphine;

MOM for methoxymethyl;

Boc for t-butoxycarbonyl;

Bz for benzyl;

Ph for phenyl;

POPd for dihydrogen dichlorobis(di-tert-butylphosphinito-κP)palladate(II);

TBS for tert-butyl dimethylsilyl; or

TMS for trimethylsilyl.

Synthetic Methods

The compounds and processes of the present invention will be better understood in connection with the following synthetic schemes that are illustrative of the methods by which the compounds of the invention may be prepared. All variable are as previously defined, unless specifically delineated herein.

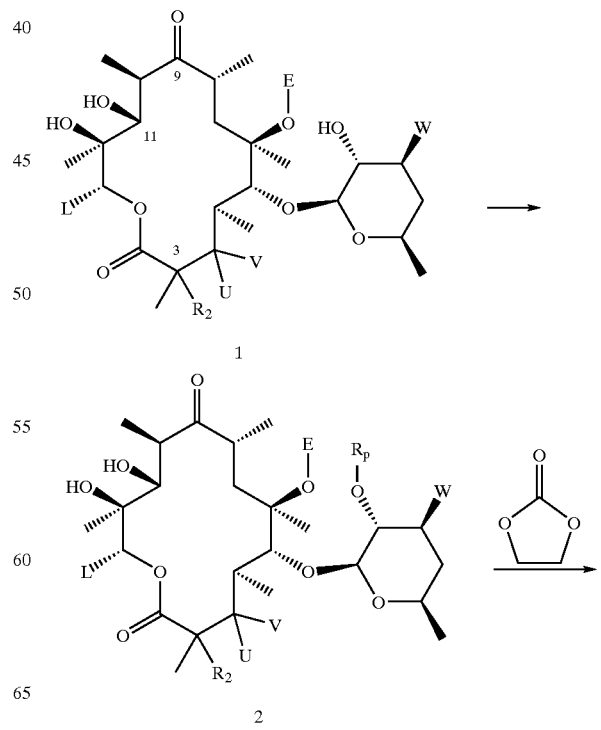

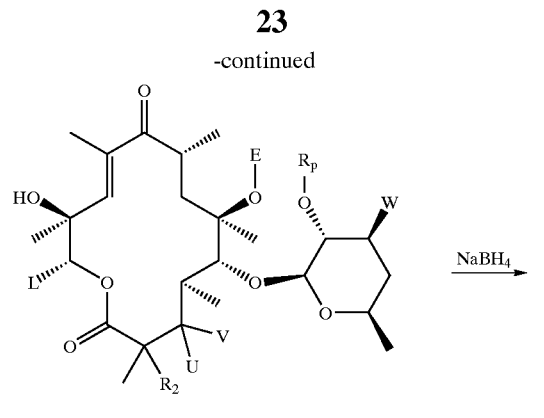

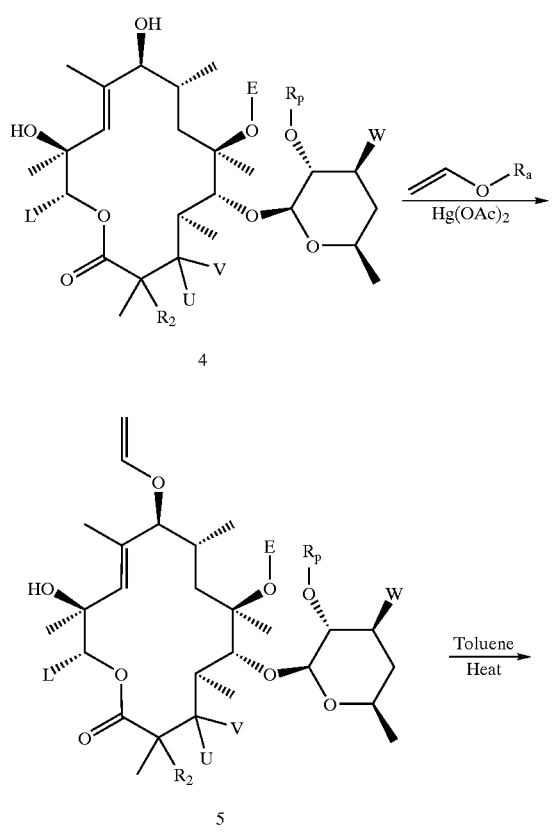

One process of the present invention for the preparation of compounds of formula I, is as shown in Scheme 1. According to this synthetic scheme, the preparation of such compounds of formula I includes the step of protecting a erythromycin derivative (compound 1 of Scheme 1) with an acid anhydride, acid chloride or a silylating reagent such as silyl chloride, HMDS, BSA and the like in an aprotic solvent such as methylene chloride, THF, chloroform, DMF, acetonitrile or the like at a temperature from about 0° C. to about 50° C. for 3–72 hours to provide compound 2. Compound 2 is treated with ethylene carbonate, either as a neat mixture or in an aprotic solvent at room temperature to about 150° C. to provide compound 3. Alternatively, compound 2 is treated with a sulfonic acid chloride or sulfonic acid anhydride in the presence of TEA, pyridine or the like in an aprotic solvent at a temperature of from about 0° C. to about 50° C. to provide the corresponding 11-O-sulfonate ester which is eliminated in a separate step by treatment with a base such as DBU, DMAP, KOt-Bu, or the like at from room temperature to about 100° C. to provide compound 3. Compound 3 further reacts with a reducing agent such as sodium borohydride, sodium triacetoxy borohydride, or the like in a protic solvent such as methanol, ethanol, isopropanol, or the like, or mixtures thereof, with an aprotic solvent such as THF, DME, or the like, at from about −20° C. to about 50° C., to provide compound 4. Alternatively, compound 3 is treated with DIBAL-H, LAH, RedAl or the like, in an aprotic solvent at from about −80° C. to about room temperature to provide compound 4. Compound 4 is alkylated selectively at the 9 oxygen by treatment with a vinyl ether, wherein $R_a$ is $C_1$–$C_6$ alkyl in the presence of a mercury (II) salt, either as a neat mixture or in an aprotic solvent, at from room temperature to about 100° C. to afford compound 5. Compound 5 is thermolyzed in an aprotic solvent such as toluene, xylene, or decahydronaphthalene at a temperature of from about 80° C. to about 200° C. for 3 to 72 hours, to afford the Claisen rearrangement product 6.

Scheme 2

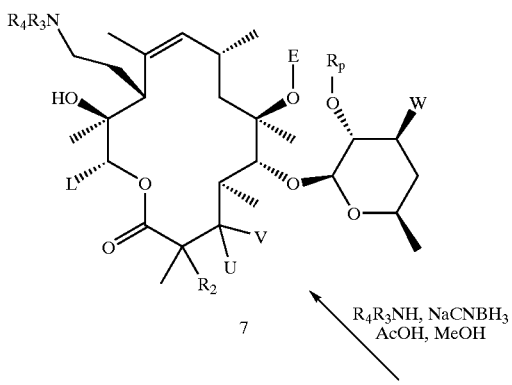

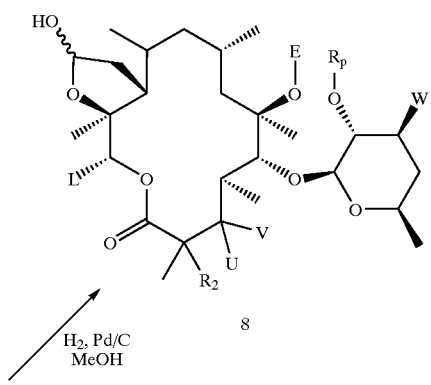

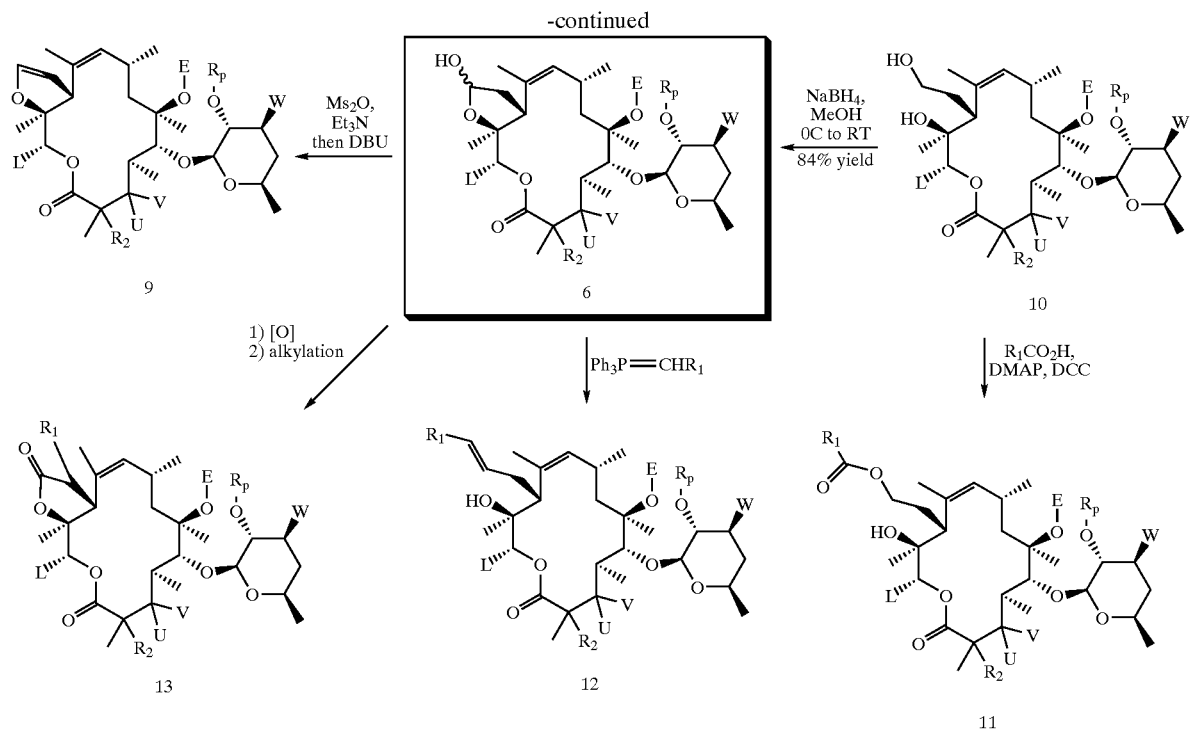

Scheme 2 illustrates further processes of the present invention for the preparation of the compounds of formulas I, II, III, and IV from compounds of formula 6 from Scheme 1. Compound of formula 6 is reacted further by reductive amination methods with primary or secondary amines in the presence of sodium cyanoborohydride or similar reducing agents, in a protic solvent such as methanol, ethanol, isopropanol, or the like, to afford compound 7.

Compounds of formula 8 may be prepared by reacting compounds of formula 6 with palladium on carbon, platinum oxide, or the like under 1–50 atm of hydrogen in an organic solvent such as methanol, ethanol, ethyl acetate or the like at a temperature of from about 0° C. to about 100° C. for 1–36 hours.

Compounds of formula 9, may be prepared by reacting the free hydroxy of formula 6 with a sulfonic anhydride, or a sulfonyl chloride in an aprotic organic solvent such as methylene chloride, ethylene chloride, THF, chloroform or the like at a temperature from about −78° C. to about 50° C. for about 30 minutes to 48 hours in the presence of an amine base, such as pyridine, diethylamine, triethylamine or the like, optionally by adding a catalyst such as DMAP, imidazole or the like, followed by treatment with a base at a temperature from 25° C. to 100° C. for about 1 hour to 48 hours. Suitable bases for this transformation include, but are not limited to, DBU, DIEA, triethylamine and the like in solvents such as acetone, DMF, or DMSO.

Compounds of formula 10 may be prepared by reducing compounds of formula 6 with sodium cyanoborohydride, lithium borohydride, or the like, in a protic solvent such as methanol, ethanol, isopropanol or the like, or mixtures thereof, in an aprotic solvent such as THF, DME, or the like, at from about −20° C. to about 50° C. Compounds of formula 10 can then be alkylated or acylated to produce compounds of formula 11, wherein $R_x$ is selected from or $C(O)R_1$. The alkylating process to provide compounds of formula 11, wherein $R_x$ is $R_1$ is performed preferably with palladium catalyzed allylation with a tert-butyl allyl carbonate or with other alkylating agents, such as, for example, an alkyl halide, alkyl sulfonate, propargyl halide, allyl halide, benzylic halide, or the like, in the presence of a base such as sodium hydride, potassium hydride, potassium tert-butoxide, potassium hydroxide, KHMDS, or the like in an aprotic solvent such as THF, DMSO, DMF, dioxane, or the like, or mixtures thereof, at a temperature of from about −20 C. to about 60° C. The acylation process to provide compounds of formula 11, wherein $R_x$ is $C(O)R_1$, involves the use of a carboxylic acid, its anhydride or mixed anhydride, an acid halide or other activated acyl derivatives, optionally with the addition of a coupling agent such as DCC or the like, and optionally with the addition of DMAP and imidazole or the like.

Compounds of formula 12, can be produced by reacting compounds of formula 6 with an alkyl, substituted alkyl, allylic, or propargylic phosphorane or phosphonate ylide in an aprotic solvent at a temperature of from about −20° C. to about 80° C. Compound 12 may optionally hydrogenated with palladium on carbon, platinum oxide, or the like under 1–4 atmospheres of hydrogen in an organic solvent such as methanol, ethanol, ethyl acetate or the like at a temperature of from about 0° C. to about 50° C. for 1–36 hours to provide the corresponding saturated linker at the C-11 position.

Compounds of formula 13, can be produced via well known means of oxidation of compounds of formula 6 followed by alkylation of said oxidized compounds. Suitable conditions for such a transformation are well known in the art.

Scheme 3

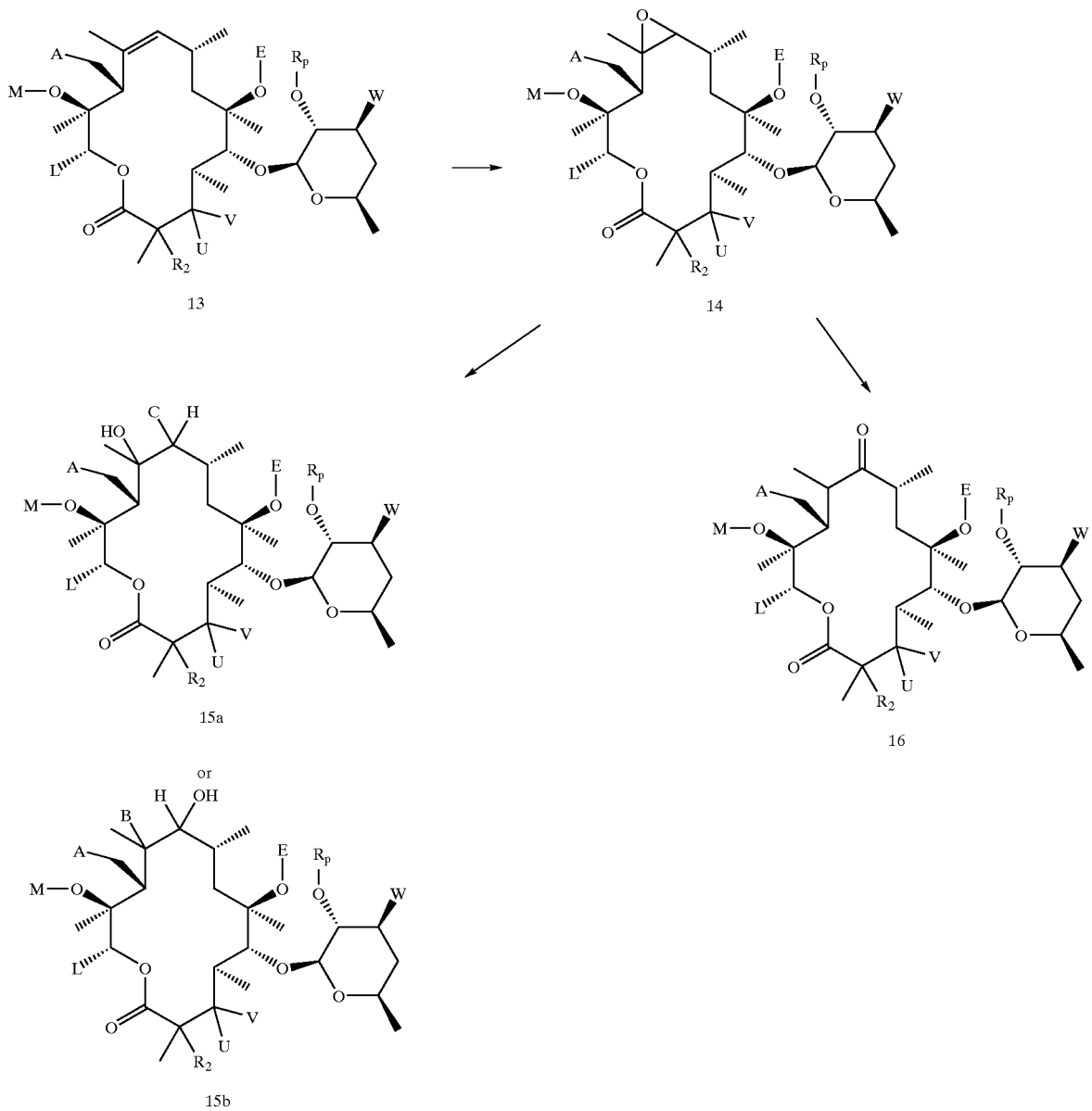

Compounds of formula 14 may be produced via reacting compounds of formula 13 with an oxidant such as m-CPBA, AcOOH, t-BuOOH or the like in an aprotic solvent. Compounds of formulas 15a and 15b may be produced by reacting a compound of formula 14 with an approprate nucleophile, such as, for example, an alkyl, allylic, propargylic or aryl cuprate, or with azide, halide or cyanide anion, and the like. Alternatively, compound 14 may be treated with a Lewis acid such as $BF_3$-etherate, $MgBr_2$-etherate, and the like, in an aprotic solvent to afford compound 16. It should be understood that compounds of formula III of the present invention, may also undergo similar transformations to produce compounds analogous to compounds 14–16 of Scheme 3.

EXAMPLES

The procedures described above for preparing the compounds of the present invention will be better understood in connection with the following examples, which are intended to be illustrative only and not limiting of the scope of the invention. Various changes and modifications to the disclosed embodiments will be apparent to those skilled in the art. Such changes and modifications, including without limitation, those relating to the chemical structures, substituents, derivatives, intermediates, syntheses, formulations and/or methods of the invention may be made without departing from the spirit of the invention and the scope of the appended claims.

Example 1

Compound of formula I: A is CHO, M, E, $R_p$, and $R_2$ are hydrogen, and U and V taken together with the carbon atom to which they are attached are C=O;

Example 2

Compound of formula I: A is $CH_2OH$, M, E, $R_p$, and $R_2$ are hydrogen, and U and V taken together with the carbon atom to which they are attached are C=O;

Example 3

Compound of formula I: A is $CH_2OCO$-[3-quinolyl], M, E, $R_p$, and $R_2$ are hydrogen, and U and V taken together with the carbon atom to which they are attached are C=O;

Example 4

Compound of formula I: A is $CH_2OCO$-[4-quinolyl], M, E, $R_p$, and $R_2$ are hydrogen, and U and V taken together with the carbon atom to which they are attached are C=O;

Example 5

Compound of formula I: A is CH=CH-phenyl, M, E, $R_p$, and $R_2$ are hydrogen, and U and V taken together with the carbon atom to which they are attached are C=O;

Example 6

Compound of formula I: A is $CH_2NH$-benzyl, M, E, $R_p$, and $R_2$ are hydrogen, and U and V taken together with the carbon atom to which they are attached are C=O;

Example 7

Compound of formula I: A is $CH_2NH$-allyl, M, E, $R_p$, and $R_2$ are hydrogen, and U and V taken together with the carbon atom to which they are attached are C=O;

Example 8

Compound of formula II: A is CHO, B is hydrogen, C is hydrogen, D is hydrogen, M, E, $R_p$, and $R_2$ are hydrogen, and U and V taken together with the carbon atom to which they are attached are C=O;

Example 9

Compound of formula II: A is CHO, B and C taken together are —O—, B is hydrogen, M, E, $R_p$, and $R_2$ are hydrogen, and U and V taken together with the carbon atom to which they are attached are C=O;

Example 10

Compound of formula II: A is CHO, B and C taken together with the carbon atom to which they are attached are C=O, D is hydrogen, M, E, $R_p$, and $R_2$ are hydrogen, and U and V taken together with the carbon atom to which they are attached are C=O;

Example 11

Compound of formula II: A is CHO, B is OH, C is hydrogen, D is OH, M, E, $R_p$, and $R_2$ are hydrogen;

Example 12

Compound of formula II: A is $CH_2OH$, B is hydrogen, C is hydrogen, D is hydrogen, M, E, $R_p$, and $R_2$ are hydrogen, and U and V taken together with the carbon atom to which they are attached are C=O;

Example 13

Compound of formula II: A is $CH_2OH$, B and C taken together are —O—, C is hydrogen, M, E, $R_p$, and $R_2$ are hydrogen, and U and V taken together with the carbon atom to which they are attached are C=O;

Example 14

Compound of formula II: A is $CH_2OH$, C and D taken together with the carbon atoms to which they are attached are C=O, B is hydrogen, M, E, $R_p$, and $R_2$ are hydrogen, and U and V taken together with the carbon atom to which they are attached are C=O;

Example 15

Compound of formula II: A is $CH_2OH$, B is OH, C is hydrogen, D is OH, M, E, $R_p$, and $R_2$ are hydrogen, and U and V taken together with the carbon atom to which they are attached are C=O;

Example 16

Compound of formula II: A is $CH_2OCO$-[3-quinolyl], B is hydrogen, C is hydrogen, D is hydrogen, M, E, $R_p$, and $R_2$ are hydrogen, and U and V taken together with the carbon atom to which they are attached are C=O;

Example 17

Compound of formula II: A is $CH_2OCO$-[3-quinolyl], B and C taken together are —O—, C is hydrogen, M, E, $R_p$, and $R_2$ are hydrogen, and U and V taken together with the carbon atom to which they are attached are C=O;

Example 18

Compound of formula II: A is $CH_2OCO$-[3-quinolyl], C and D taken together with the carbon atom to which they are attached are C=O, B is hydrogen, M, E, $R_p$, and $R_H$ are hydrogen;

Example 19

Compound of formula II: A is $CH_2OCO$-[3-quinolyl], B is OH, C is hydrogen, D is OH, M, E, $R_p$, and $R_2$ are hydrogen, and U and V taken together with the carbon atom to which they are attached are C=O;

Example 20

Compound of formula II: A is $CH_2OCO$-[4-quinolyl], B is hydrogen, C is hydrogen, D is hydrogen, M, E, $R_p$, and $R_2$ are hydrogen, and U and V taken together with the carbon atom to which they are attached are C=O;

Example 21

Compound of formula II: A is $CH_2OCO$-[4-quinolyl], B and C taken together are —O—, C is hydrogen, M, E, $R_p$, and $R_2$ are hydrogen, and U and V taken together with the carbon atom to which they are attached are C=O;

Example 22

Compound of formula II: A is $CH_2OCO$-[4-quinolyl], C and D taken together with the carbon atom to which they are attached are C=O, B is hydrogen M, E, $R_p$, and $R_H$ are hydrogen, and U and V taken together with the carbon atom to which they are attached are C=O;

Example 23

Compound of formula II: A is $CH_2OCO$-[4-quinolyl], B is OH, C is hydrogen, D is OH, M, E, $R_p$, and $R_2$ are hydrogen, and U and V taken together with the carbon atom to which they are attached are C=O;

Example 24

Compound of formula II: A is CH=CH-phenyl, B is hydrogen, C is hydrogen, D is hydrogen, M, E, $R_p$, and $R_2$ are hydrogen, and U and V taken together with the carbon atom to which they are attached are C=O;

Example 25

Compound of formula II: A is $CH_2$NH-benzyl, B is hydrogen, C is hydrogen, D is hydrogen, M, E, $R_p$, and $R_2$ are hydrogen, and U and V taken together with the carbon atom to which they are attached are C=O;

Example 26

Compound of formula II: A is $CH_2$NH-benzyl, B and C taken together are —O—, C is hydrogen, M, E, $R_p$, and $R_2$ are hydrogen, and U and V taken together with the carbon atom to which they are attached are C=O;

Example 27

Compound of formula II: A is $CH_2$NH-benzyl, B and C taken together with the carbon atom to which they are attached are C=O, D is hydrogen, M, E, $R_p$, and $R_2$ are hydrogen, and U and V taken together with the carbon atom to which they are attached are C=O;

Example 28

Compound of formula II: A is $CH_2$NH-benzyl, B is OH, C is hydrogen, D is OH, M, E, $R_p$, and $R_2$ are hydrogen, and U and V taken together with the carbon atom to which they are attached are C=O;

Example 29

Compound of formula II: A is $CH_2$NH-allyl, B is hydrogen, C is hydrogen, D is hydrogen, M, E, $R_p$, and $R_2$ are hydrogen, and U and V taken together with the carbon atom to which they are attached are C=O;

Example 30

Compound of formula II: A is $CH_2$NH-allyl, B and C taken together are —O—, C is hydrogen, M, E, $R_p$, and $R_2$ are hydrogen, and U and V taken together with the carbon atom to which they are attached are C=O;

Example 31

Compound of formula II: A is $CH_2$NH-allyl, C and D taken together with the carbon atom to which they are attached are C=O, B is hydrogen, M, E, $R_p$, and $R_2$ are hydrogen, and U and V taken together with the carbon atom to which they are attached are C=O;

Example 32

Compound of formula II: A is $CH_2$NH-allyl, B is OH, C is hydrogen, D is OH, M, E, $R_p$, and $R_2$ are hydrogen, and U and V taken together with the carbon atom to which they are attached are C=O; and

Example 33

Compound of formula II or IV: B is OH, C is hydrogen, D is OH, U and V taken together with the carbon atom to which they are attached are C=O, X and Y taken together with the carbon atom to which they are attached are C=O, and M, E, $R_p$, $R_2$, X', and Y' are hydrogen.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound of formula I, II, III, or IV:

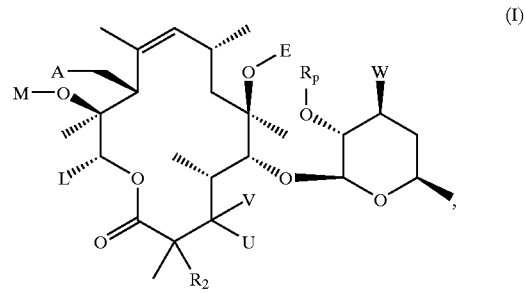
(I)

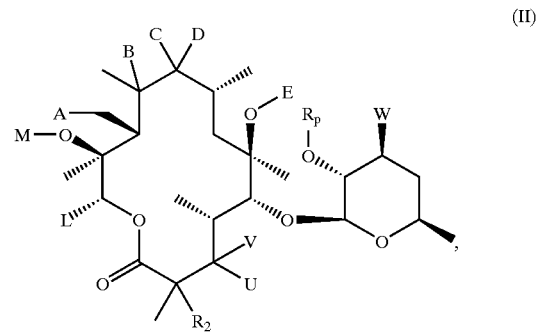
(II)

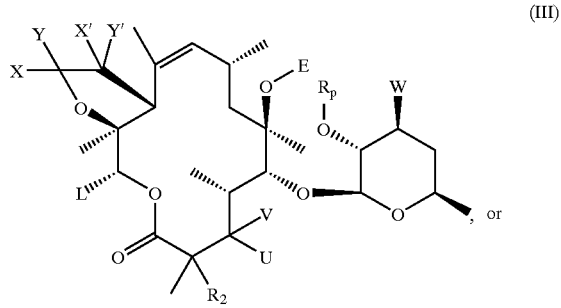
(III)

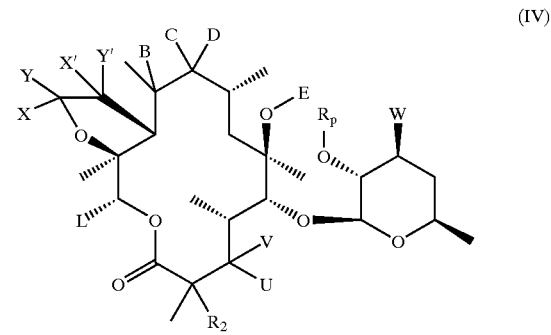
(IV)

or their racemates, enantiomers, regioisomers, salts, esters or prodrugs thereof, wherein A is independently selected from $R_1$, —CH($R_{A1}$)($R_{A2}$);

Each B, C, and D is independently selected from deuterium, halogen, $R_1$, $OR_1$, $S(O)_nR_1$, —$NR_1C(O)R_1$, —$NR_1C(O)NR_3R_4$, —$NR_1S(O)_nR_1$, —$C(O)NR_3R_4$, and —$NR_3R_4$;

or B and C taken together are selected from —O—, —S—, —N($R_1$)—, a substituted or unsubstituted alicyclic group, or a substituted or unsubstituted heterocyclic group;

or C and D taken together with the carbon atom to which they are attached are selected CO, C=CHR$_1$, C=NR$_1$, C=NOR$_1$, C=NO(CH$_2$)$_m$R$_1$, C=NNHR$_1$, C=NNHCOR$_1$, C=NNHCONR$_3$R$_4$, C=NNHS(O)$_n$R$_1$, C=N—N=CHR$_1$;

E is independently selected from $R_1$ with the proviso that for formula I or formula II, E is not methyl;

Each $R_1$ is independently selected from the group consisting of: hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

Each of $R_3$ and $R_4$ is independently selected from the group consisting of: hydrogen, acyl a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a substituted, or unsubstituted heterocyclic group; or can be taken together with the nitrogen atom to which they are attached to form a substituted or unsubstituted heterocyclic or heteroaromatic ring;

Each $R_{A1}$ and $R_{A2}$ are independently selected from hydrogen, deuterium, halogen, $R_1$, OR$_1$, S(O)$_n$R$_1$, —NR$_1$C(O)R$_1$, —NR$_1$C(O)NR$_3$R$_4$, —NHS(O)$_n$R$_1$, —CONR$_3$R$_4$, and NR$_3$R$_4$;

or $R_{A1}$ and $R_{A2}$, taken together with the carbon atom to which they are attached, form a substituted or unsubstituted alicyclic, aromatic, heterocyclic or heteroaromatic ring;

or $R_{A1}$ and $R_{A2}$ taken together with the carbon atom to which they are attached are selected from C=O, C=CHR$_1$, C=NR$_1$, C=NOR$_1$, C=NO(CH$_2$)$_m$R$_1$, C=NNHR$_1$, C=NNHCOR$_1$, C=NNHCONR$_3$R$_4$, C=NNHS(O)$_n$R$_1$, C=N—N=CHR$_1$;

M is selected from the group consisting of: $R_1$, C(O)R$_1$, S(O)$_n$R$_1$ or C(O)NR$_3$R$_4$;

L is selected from the group consisting of: hydrogen, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

X, Y, X', and Y' are independently selected from the group consisting of: deuterium, halogen, $R_1$, OR$_1$, S(O)$_n$R$_1$, —NR$_1$C(O)R$_1$, —NR$_1$C(O)NR$_3$R$_4$, —NR$_1$S(O)$_n$R$_1$, —C(O)NR$_3$R$_4$, and —NR$_3$R$_4$;

or X and Y, taken together with the carbon atom to which they are attached, are C=O;

or X and X', taken together with the carbon atoms to which they are attached, are C=C;

one of U or V is hydrogen and the other is independently selected from the group consisting of: $R_1$, OR$_1$, OC(O) R$_1$, OC(O)NR$_3$R$_4$, S(O)$_n$R$_1$, or

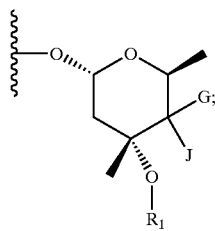

or U and V, taken together with the carbon atom to which they are attached, are C=O;

one of J or G is hydrogen and the other is selected from: $R_1$, OR$_1$, or NR$_3$R$_4$;

or, J and G, taken together with the carbon atom to which they are attached, are selected from: C=O, C=NR$_1$, C=NOR$_1$, C=NO(CH$_2$)$_m$R$_1$, C=NNHR$_1$, C=NNHCOR$_1$, C=NNHCONR$_1$R$_2$, C=NNHS(O)$_n$R$_1$, or C=N—N=CHR$_1$;

W is NR$_3$R$_4$;

$R_2$ is selected from hydrogen, alkyl or halogen;

$R_p$ is selected from hydrogen and a hydroxy protecting group;

m is an integer; and n is 0, 1, or 2.

2. A compound of claim 1, wherein E is hydrogen.

3. A compound of formula I or II according to claim 1, wherein A is CHO.

4. A compound of claim 1, wherein X is hydrogen, Y is hydroxyl, X' is hydrogen and Y' is hydrogen.

5. A compound of claim 1, wherein C and D taken together with the carbon atom to which they are attached are C=O.

6. A compound of formula III or IV according to claim 1, wherein X and Y taken together with the carbon atom to which they are attached are C=O.

7. A compound of formula claim 1, wherein E is CH$_2$CH=CH$_2$.

8. A compound of formula claim 1, wherein W is N(CH$_3$)$_2$.

9. A compound of claim 1, wherein L is ethyl.

10. A compound of claim 1, wherein U and V taken together with the carbon atom to which they are attached are C=O.

11. A compound of formula II Or IV according to claim 1.

12. A compound of formula II or IV according to claim 1, wherein U and V taken together with the carbon atom to which they are attached are C=O.

13. A compound of claim 1, selected from:
   a. Compound of formula I: A is CHO, M, E, $R_p$, and $R_2$ are hydrogen, and U and V taken together with the carbon atom to which they are attached are C=O;
   b. Compound of formula I: A is CH$_2$OH, M, E, $R_p$, and $R_2$ are hydrogen, and U and V taken together with the carbon atom to which they are attached are C=O;
   c. Compound of formula I: A is CH$_2$OCO-[3-quinolyl], M, E, $R_p$, and $R_2$ are hydrogen, and U and V taken together with the carbon atom to which they are attached are C=O;
   d. Compound of formula I: A is CH$_2$OCO-[4-quinolyl], M, E, $R_p$, and $R_2$ are hydrogen, and U and V taken together with the carbon atom to which they are attached are C=O;

e. Compound of formula I: A is CH=CH-phenyl, M, E, $R_p$, and $R_2$ are hydrogen, and U and V taken together with the carbon atom to which they are attached are C=O;

f. Compound of formula I: A is CH$_2$NH-benzyl, M, E, $R_p$, and $R_2$ are hydrogen, and U and V taken together with the carbon atom to which they are attached are C=O;

g. Compound of formula I: A is CH$_2$NH-allyl, M, E, $R_p$ and $R_2$ are hydrogen, and U and V taken together with the carbon atom to which they are attached are C=O;

h. Compound of formula II; A is CHO, B is hydrogen, C is hydrogen, D is hydrogen, M, E, $R_p$, and $R_2$ are hydrogen, and U and V taken together with the carbon atom to which they are attached are C=O;

i. Compound of formula II: A is CHO, B and C taken together are —O—, B is hydrogen, M E, $R_p$, and $R_2$ are hydrogen, and U and V taken together with the carbon atom to which they are attached are C=O;

j. Compound of formula II: A is CHO, B and C taken together with the carbon atom to which they are attached are C=O, D is hydrogen, M, E, $R_p$, and $R_2$ are hydrogen, and U and V taken together with the carbon atom to which they are attached are C=O;

k. Compound of formula II: A is CHO, B is OH, C is hydrogen, D is OH, M, E, $R_p$, and $R_2$ are hydrogen;

l. Compound of formula II: A is CH$_2$OH, B is hydrogen, C is hydrogen, D is hydrogen, M, E, $R_p$, and $R_2$ are hydrogen, and U and V taken together with the carbon atom to which they are attached are C=O;

m. Compound of formula II: A is CH$_2$OH, B and C taken together are —O—, C is hydrogen, M, E, $R_p$, and $R_2$ are hydrogen, and U and V taken together with the carbon atom to which they are attached are C=O;

n. Compound of formula II: A is CH$_2$OH, C and D taken together with the carbon atoms to which they are attached are C=O, B is hydrogen, M, E, $R_p$, and $R_2$ are hydrogen, and U and V taken together with the carbon atom to which they are attached are C=O;

o. Compound of formula II: A is CH$_2$OH, B is OH, C is hydrogen, D is OH, M, E, $R_p$, and $R_2$ are hydrogen, and U and V taken together with the carbon atom to which they are attached are C=O;

p. Compound of formula II: A is CH$_2$OCO-[3-quinolyl], B is hydrogen, C is hydrogen, D is hydrogen, M, E, $R_p$, and $R_2$ are hydrogen, and U and V taken together with the carbon atom to which they are attached are C=O;

q. Compound of formula II: A is CH$_2$OCO-[3-quinolyl], B and C taken together are —O—, C is hydrogen, M, E, $R_p$, and $R_2$ are hydrogen, and U and V taken together with the carbon atom to which they are attached are C=O;

r. Compound of formula II: A is CH$_2$OCO-[3-quinolyl], C and D taken together with the carbon atom to which they are attached are C=O, B is hydrogen, M, E, $R_p$, and $R_H$ are hydrogen;

s. Compound of formula II: A is CH$_2$OCO-[3-quinolyl], B is OH, C is hydrogen, D is OH, M, E, $R_p$, and $R_2$ are hydrogen, and U and V taken together with the carbon atom to which they are attached are C=O;

t. Compound of formula II: A is CH$_2$OCO-[4-quinolyl], B is hydrogen, C is hydrogen, D is hydrogen, M, E, $R_p$, and $R_2$ are hydrogen, and U and V taken together with the carbon atom to which they are attached are C=O;

u. Compound of formula II: A is CH$_2$OCO-[4-quinolyl], B and C taken together are —O—, C is hydrogen, M, E, $R_p$, and $R_2$ are hydrogen, and U and V taken together with the carbon atom to which they are attached are C=O;

v. Compound of formula II: A is CH$_2$OCO-[4-quinolyl], C and D taken together with the carbon atom to which they are attached are C=O, B is hydrogen M, E, $R_p$, and $R_H$ are hydrogen, and U and V taken together with the carbon atom to which they are attached are C=O;

w. Compound of formula II: A is CH$_2$OCO-[4-quinolyl], B is OH, C is hydrogen, D is OH, M, E, $R_p$, and $R_2$ are hydrogen, and U and V taken together with the carbon atom to which they are attached are C=O;

x. Compound of formula II: A is CH=CH-phenyl, B is hydrogen, C is hydrogen, D is hydrogen, M, E, $R_p$, and $R_2$ are hydrogen, and U and V taken together with the carbon atom to which they are attached are C=O;

y. Compound of formula II: A is CH$_2$NH-benzyl, B is hydrogen, C is hydrogen, D is hydrogen, M, E, $R_p$, and $R_2$ are hydrogen, and U and V taken together with the carbon atom to which they are attached are C=O;

z. Compound of formula II: A is CH$_2$NH-benzyl, B and C taken together are —O—, C is hydrogen, M, E, $R_p$, and $R_2$ are hydrogen, and U and V taken together with the carbon atom to which they are attached are C=O;

aa. Compound of formula II: A is CH$_2$NH-benzyl, B and C taken together with the carbon atom to which they are attached are C=O, D is hydrogen, M, E, $R_p$, and $R_2$ are hydrogen, and U and V taken together with the carbon atom to which they are attached are C=O;

bb. Compound of formula II: A is CH$_2$NH-benzyl, B is OH, C is hydrogen, D is OH, M, E, $R_p$, and $R_2$ are hydrogen, and U and V taken together with the carbon atom to which they are attached are C=O;

cc. Compound of formula II: A is CH$_2$NH-allyl, B is hydrogen, C is hydrogen, D is hydrogen, M, E, $R_p$, and $R_2$ are hydrogen, and U and V taken together with the carbon atom to which they are attached are C=O;

dd. Compound of formula II: A is CH$_2$NH-allyl, B and C taken together are —O—, C is hydrogen, M, E, $R_p$, and $R_2$ are hydrogen, and U and V taken together with the carbon atom to which they are attached are C=O;

ee. Compound of formula II: A is CH$_2$NH-allyl, C and D taken together with the carbon atom to which they are attached are C=O, B is hydrogen, M, E, $R_p$, and $R_2$ are hydrogen, and U and V taken together with the carbon atom to which they are attached are C=O; or ff. Compound of formula II: A is CH$_2$NH-allyl, B is OH, C is hydrogen, D is OH, M, E, $R_p$, and $R_2$ are hydrogen, and U and V taken together with the carbon atom to which they are attached are C=O; or gg. Compound of formula II or IV; B is OH, C is hydrogen, D is OH, U and V taken together with the carbon atom to which they are attached are C=O, X and Y taken together with the carbon atom to which they are attached are C=O, and M, E, $R_p$, $R_2$, X', and Y' are hydrogen.

14. A pharmaceutical composition comprising a therapeutically acceptable amount of a compound of claim 1, optionally in combination with a pharmaceutically acceptable carrier or excipient.

15. A method of treating a bacterial infection in a subject in need of such treatment comprising the step of administering a pharmaceutical composition of claim 14.

* * * * *